United States Patent
Sato et al.

(10) Patent No.: US 8,273,521 B2
(45) Date of Patent: Sep. 25, 2012

(54) RADIATION-SENSITIVE RESIN COMPOSITION AND COMPOUND

(75) Inventors: Mitsuo Sato, Tokyo (JP); Kazuo Nakahara, Tokyo (JP); Hiromitsu Nakashima, Tokyo (JP); Takanori Nakano, Tokyo (JP); Makoto Sugiura, Tokyo (JP)

(73) Assignee: JSR Corporation, Tokyo (JP)

( * ) Notice: Subject to any disclaimer, the term of this patent is extended or adjusted under 35 U.S.C. 154(b) by 181 days.

(21) Appl. No.: 12/846,836

(22) Filed: Jul. 30, 2010

(65) Prior Publication Data

US 2011/0027718 A1 Feb. 3, 2011

(30) Foreign Application Priority Data

Jul. 31, 2009 (JP) .................................. 2009-178640
Sep. 24, 2009 (JP) .................................. 2009-219746

(51) Int. Cl.
*G03F 7/00* (2006.01)
*G03F 7/004* (2006.01)
*G03F 7/028* (2006.01)

(52) U.S. Cl. ........................ 430/270.1; 430/919; 430/920

(58) Field of Classification Search ............... 430/270.1, 430/919, 920
See application file for complete search history.

(56) References Cited

U.S. PATENT DOCUMENTS

| | | | |
|---|---|---|---|
| 6,448,352 B1 * | 9/2002 | Jung et al. ................. | 526/264 |
| 2007/0269734 A1 | 11/2007 | Kimura et al. | |
| 2008/0038661 A1 | 2/2008 | Chiba et al. | |
| 2010/0151388 A1 * | 6/2010 | Yang et al. ................. | 430/285.1 |
| 2010/0304297 A1 * | 12/2010 | Hatakeyama et al. ..... | 430/270.1 |
| 2011/0033803 A1 * | 2/2011 | Hatakeyama et al. ..... | 430/285.1 |

FOREIGN PATENT DOCUMENTS

| | | | |
|---|---|---|---|
| EP | 0523957 | | 1/1993 |
| EP | 0558280 | | 9/1993 |
| JP | 5-158239 | | 6/1993 |
| JP | 05-232706 | | 9/1993 |
| JP | 5-249683 | | 9/1993 |
| JP | 2001-166476 | | 6/2001 |
| JP | 2001166476 A | * | 6/2001 |
| JP | 2001-215689 | | 8/2001 |
| JP | 2006-227632 | | 8/2006 |
| JP | 2011048175 A | * | 3/2011 |
| WO | WO 2005/069076 | | 7/2005 |
| WO | WO 2006/035790 | | 4/2006 |

OTHER PUBLICATIONS

Machine translation of JP 2001-166476 (no date).*

* cited by examiner

*Primary Examiner* — Amanda C. Walke
(74) *Attorney, Agent, or Firm* — Ditthavong Mori & Steiner, P.C.

(57) ABSTRACT

A radiation-sensitive resin composition includes a compound shown by a formula (1) in which $R^1$ represents a divalent hydrocarbon group having 1 to 20 carbon atoms and $R^2$ represents a hydrogen atom or a monovalent hydrocarbon group having 1 to 20 carbon atoms, or $R^1$ and $R^2$ form a heterocyclic structure having 4 to 20 carbon atoms, $R^3$ represents a monovalent acid-dissociable group, n is an integer from 1 to 6, each of $R^{4A}$, $R^{4B}$, and $R^{4C}$ represents one of an alkyl group having 1 to 4 carbon atoms and a monovalent alicyclic hydrocarbon group having 4 to 20 carbon atoms, or $R^{4A}$ represents one of an alkyl group having 1 to 4 carbon atoms and a monovalent alicyclic hydrocarbon group having 4 to 20 carbon atoms and $R^{4B}$ and $R^{4C}$ form a divalent alicyclic hydrocarbon group having 4 to 20 carbon atoms.

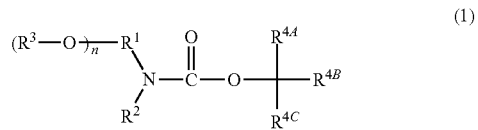

(1)

10 Claims, No Drawings

RADIATION-SENSITIVE RESIN COMPOSITION AND COMPOUND

CROSS-REFERENCE TO RELATED APPLICATION

The present application claims priority to Japanese Patent Application No. 2009-178640, filed Jul. 31, 2009 and Japanese Patent Application No. 2009-219746, filed Sep. 24, 2009. The contents of these applications are incorporated herein by reference in their entirety.

BACKGROUND OF THE INVENTION

1. Field of the Invention

The present invention relates to a radiation-sensitive resin composition and a compound.

2. Discussion of the Background

A chemically-amplified radiation-sensitive resin composition generates an acid upon exposure to deep ultraviolet rays (e.g., KrF excimer laser light or ArF excimer laser light) or electron beams. A difference in dissolution rate in a developer occurs between the exposed area and the unexposed area due to chemical reactions catalyzed by the acid, so that a resist pattern is formed on a substrate.

For example, a resin composition that includes a polymer including an alicyclic hydrocarbon that does not have a high absorbance at 193 nm in its skeleton (particularly a polymer including a lactone skeleton in its repeating unit) has been used as a lithography material when using an ArF excimer laser that enables microfabrication at a shorter wavelength as a light source.

A nitrogen-containing compound is added to such a radiation-sensitive resin composition in order to obtain process stability (see Japanese Patent Application Publications (KOKAI) No. 5-232706, No. 5-249683, and No. 5-158239). A nitrogen compound that includes a specific carbamate group may be added to improve the lithographic performance of an isolated pattern (see Japanese Patent Application Publications (KOKAI) No. 2001-166476 and No. 2001-215689).

SUMMARY OF THE INVENTION

According to one aspect of the invention, a radiation-sensitive resin composition includes (A) a compound, (B) a resin, and (C) a photoacid generator. The compound (A) is shown by a formula (1). The resin (B) is protected by an acid-dissociable group. The resin (B) is insoluble or scarcely soluble in alkali, and becomes alkali-soluble upon dissociation of the acid-dissociable group.

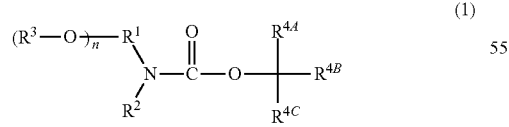

(1)

$R^1$ represents a divalent hydrocarbon group having 1 to 20 carbon atoms and $R^2$ represents a hydrogen atom or a monovalent hydrocarbon group having 1 to 20 carbon atoms, or $R^1$ and $R^2$ are such that $R^1$ and $R^2$ together with a nitrogen atom form a heterocyclic structure having 4 to 20 carbon atoms if $R^1$ and $R^2$ bond with each other via the nitrogen atom. $R^3$ represents a monovalent acid-dissociable group, n is an integer from 1 to 6. Each of $R^{4A}$, $R^{4B}$, and $R^{4C}$ represents one of an alkyl group having 1 to 4 carbon atoms and a monovalent alicyclic hydrocarbon group having 4 to 20 carbon atoms, or $R^{4A}$ represents one of an alkyl group having 1 to 4 carbon atoms and a monovalent alicyclic hydrocarbon group having 4 to 20 carbon atoms and $R^{4B}$ and $R^{4C}$ are such that $R^{4B}$ and $R^{4C}$ together with a carbon atom form a divalent alicyclic hydrocarbon group having 4 to 20 carbon atoms if $R^{4B}$ and $R^{4C}$ bond with each other via the carbon atom.

According to another aspect of the invention, a compound is shown by a formula (1).

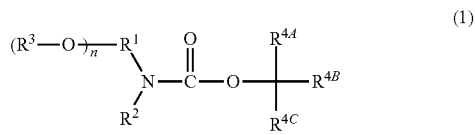

(1)

$R^1$ represents a represents a divalent hydrocarbon group having 1 to 20 carbon atoms and $R^2$ represents a hydrogen atom or a monovalent hydrocarbon group having 1 to 20 carbon atoms, or $R^1$ and $R^2$ are such that $R^1$ and $R^2$ together with a nitrogen atom form a heterocyclic structure having 4 to 20 carbon atoms if $R^1$ and $R^2$ bond with each other via the nitrogen atom. $R^3$ represents a monovalent acid-dissociable group, n is an integer from 1 to 6. Each of $R^{4A}$, $R^{4B}$, and $R^{4C}$ represents one of an alkyl group having 1 to 4 carbon atoms and a monovalent alicyclic hydrocarbon group having 4 to 20 carbon atoms, or $R^{4A}$ represents one of an alkyl group having 1 to 4 carbon atoms and a monovalent alicyclic hydrocarbon group having 4 to 20 carbon atoms and $R^{4B}$ and $R^{4C}$ are such that $R^{4B}$ and $R^{4C}$ together with a carbon atom form a divalent alicyclic hydrocarbon group having 4 to 20 carbon atoms if $R^{4B}$ and $R^{4C}$ bond with each other via the carbon atom.

DESCRIPTION OF THE EMBODIMENTS

Embodiments of the invention are described below. Note that the invention is not limited to the following embodiments.

In the radiation-sensitive resin composition according to an embodiment of the invention, the group represented by —$CR^{4A}R^{4B}R^{4C}$ in the formula (1) is preferably a tert-butyl group or a tert-amyl group.

In the radiation-sensitive resin composition according to one embodiment of the invention, $R^3$ in the formula (1) is preferably at least one group selected from groups shown by the following formulas (1-1) to (1-3),

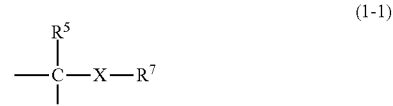

(1-1)

(1-2)

(1-3)

wherein X represents an oxygen atom or a sulfur atom, each of $R^5$ and $R^6$ represents one of a hydrogen atom, an alkyl group having 1 to 20 carbon atoms, and an alkoxy group having 1 to 20 carbon atoms, and each of $R^7$, $R^8$, and $R^9$ represents one of an alkyl group having 1 to 20 carbon atoms, an alkoxyalkyl group having 2 to 20 carbon atoms, an alicyclic hydrocarbon hydrocarbon group having 3 to 20 carbon atoms, an aryl group having 6 to 18 carbon atoms, and an aralkyl group having 7 to 19 carbon atoms, provided that $R^5$ and $R^7$ may bond to form a heterocyclic structure having 3 to 20 carbon atoms together with the carbon atom that is bonded to $R^5$ and X that is bonded to $R^7$.

In the radiation-sensitive resin composition according to one embodiment of the invention, the resin (B) preferably includes a repeating unit shown by the following formula (2),

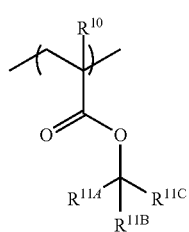

(2)

wherein $R^{10}$ represents a hydrogen atom or a methyl group, and wherein each of $R^{11A}$, $R^{11B}$, and $R^{11C}$ represents one of a linear or branched alkyl group having 1 to 4 carbon atoms and an alicyclic hydrocarbon group having 4 to 20 carbon atoms, or $R^{11A}$ represents one of a linear or branched alkyl group having 1 to 4 carbon atoms and an alicyclic hydrocarbon group having 4 to 20 carbon atoms and $R^{11B}$ and $R^{11C}$ are such that $R^{11B}$ and $R^{11C}$ together with a carbon atom form an alicyclic hydrocarbon group having 4 to 20 carbon atoms if $R^{11B}$ and $R^{11C}$ bond with each other via the carbon atom.

The radiation-sensitive resin composition according to the embodiments of the invention may be used as a chemically-amplified resist material that exhibits improved MEEF performance in addition to excellent sensitivity, resolution, and exposure margin.

Compound (A)

The compound (A) is a low-molecular-weight compound shown by the formula (1). The compound (A) includes two types of acid-dissociable groups in one molecule.

The group represented by $-CR^{4A}R^{4B}R^{4C}$ of the compound (A) dissociates due to an acid to form a basic amino group. It is conjectured that the basicity of the resist film is moderately controlled during post-exposure bake due to dissociation of the above group in a moderate ratio, so that the lithographic performance is improved. The group represented by $-R^3$ of the compound (A) dissociates due to an acid to form an alcohol. It is conjectured that the solubility of the resist is moderately controlled during post-exposure bake due to dissociation of $R^3$ in a moderate ratio, so that the lithographic performance is improved. The above effect is significant as compared with an amine compound in which only the basicity is controlled.

Examples of the divalent hydrocarbon group having 1 to 20 carbon atoms represented by $R^1$ in the formula (1) include divalent linear or branched hydrocarbon groups having 1 to 20 carbon atoms (e.g., methylene group, ethylene group, n-propylene group, i-propylene group, n-butylene group, n-pentylene group, n-hexylene group, n-heptylene group, n-octylene group, n-nonylene group, and n-decylene group); divalent alicyclic hydrocarbon groups having 3 to 20 carbon atoms (e.g., cyclobutylene group, cyclopentylene group, cyclohexylene group, cyclooctylene group, norbornylane group, tricyclodecylene group, tetracyclododecylene group, and adamantylene group); arylene groups having 6 to 20 carbon atoms (e.g., phenylene group and naphthylene group); aralkylene groups having 7 to 20 carbon atoms (e.g., benzylene group, phenylethylene group, phenylpropylene group, naphthylmethylene group, and naphthylethylene group); and the like. Among these, groups having 4 or more carbon atoms are preferable.

Examples of the monovalent hydrocarbon group having 1 to 20 carbon atoms (preferably 4 or more carbon atoms) represented by $R^2$ include linear or branched alkyl groups (e.g., n-butyl group, n-pentyl group, n-hexyl group, n-heptyl group, n-octyl group, n-nonyl group, and n-decyl group); alicyclic hydrocarbon groups (e.g., cyclobutyl group, cyclopentyl group, cyclohexyl group, cyclooctyl group, norbornyl group, tricyclodecyl group, tetracyclododecyl group, and adamantyl group); aryl groups (e.g., phenyl group and naphthyl group); and aralkyl groups (e.g., benzyl group, phenylethyl group, phenylpropyl group, naphthylmethyl group, and naphthylethyl group). These groups may be substituted with a group (e.g., hydroxyl group, carboxyl group, carbonyl group, nitro group, amino group, silyl group, halogen atom, or thienyl group) other than a hydrocarbon group.

Examples of the heterocyclic structure having 4 to 20 atoms formed by $R^1$ and $R^2$ together with the nitrogen atom that is bonded to $R^1$ and $R^2$ include a pyrrole structure, an imidazole structure, a pyrazole structure, a pyridine structure, a pyridazine structure, a pyrimidine structure, a pyrazine structure, a piperidine structure, a pyrrolidine structure, a piperazine structure, a morpholine structure, and the like. At least one hydrogen atom of these structures may be substituted with a linear or branched hydrocarbon group.

The acid-dissociable group represented by $R^3$ is not particularly limited insofar as that the acid-dissociable group dissociates due to an acid so that $-OR^3$ becomes $-OH$. The group shown by the formulas (1-1) to (1-3) are particularly preferable as the acid-dissociable group.

Examples of the alkyl group having 1 to 20 carbon atoms represented by $R^5$ and $R^6$ in the formula (1-1) include a methyl group, an ethyl group, an n-propyl group, and the like. Examples of the alkoxy group having 1 to 20 carbon atoms include a methoxy group, an ethoxy group, an n-propoxy group, and the like. These groups may be substituted with a hydroxyl group, a carboxyl group, a carbonyl group, a nitro group, an amino group, a silyl group, a halogen atom, a thienyl group, or the like.

Examples of the alkyl group having 1 to 20 carbon atoms represented by $R^7$, $R^8$, and $R^9$ in the formulas (1-1) to (1-3) include a methyl group, an ethyl group, an n-propyl group, a tert-butyl group, and the like. Examples of the alkoxyalkyl group having 2 to 20 carbon atoms include a methoxymethyl group, a methoxyethyl group, an ethoxymethyl group, an ethoxyethyl group, a methoxypropyl group, an ethoxypropyl group, a propoxymethyl group, a propoxyethyl group, and the like. Examples of the alicyclic hydrocarbon group having 3 to 20 carbon atoms include a cyclobutyl group, a cyclopentyl group, a cyclohexyl group, a cyclooctyl group, a norbornyl group, a tricyclodecyl group, a tetracyclododecyl group, an adamantyl group, and the like. Examples of the aryl group include a phenyl group, a naphthyl group, and the like. Examples of the aralkyl group include a benzyl group, a phenylethyl group, a phenylpropyl group, a naphthylmethyl group, a naphthylethyl group, and the like. These groups may be substituted with a hydroxyl group, a carboxyl group, a carbonyl group, a nitro group, an amino group, a silyl group, a halogen atom, a thienyl group, or the like.

Examples of the heterocyclic structure formed by $R^5$ and $R^7$ together with the carbon atom that is bonded to $R^5$ and X that is bonded to $R^7$ include oxygen-containing structures (e.g., oxetane, tetrahydrofuran, tetrahydropyran, dioxolane, and dioxane); sulfur-containing structures (e.g., thietane, tetrahydrothiophene, thiane, and dithiane); and the like. These structures may be substituted with any of the substituted or unsubstituted alkyl groups, alkoxy groups, and alkoxyalkyl groups mentioned above as the groups represented by $R^5$ to $R^9$, a hydroxyl group, a carboxyl group, a carbonyl group, a nitro group, an amino group, a silyl group, a halogen atom, a thienyl group, and the like.

Specific examples of the acid-dissociable group shown by the formula (1-1) include groups shown by the following formulas.

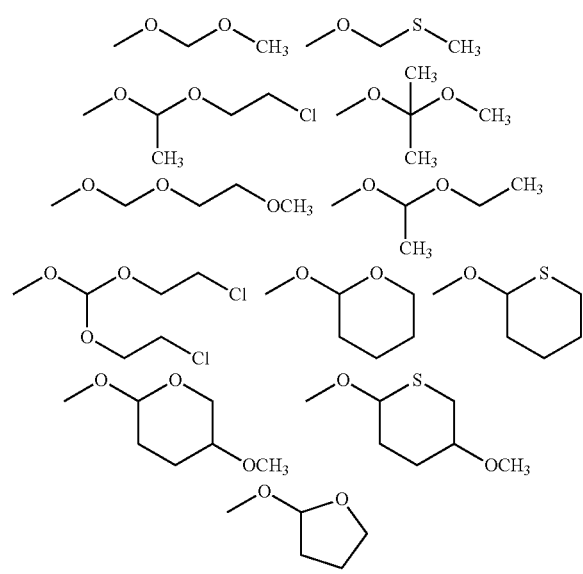

Specific examples of the acid-dissociable group shown by the formula (1-2) include a methylcarbonyloxy group, a trichloromethylcarbonyloxy group, and a tert-butoxycarbonyl group.

Specific examples of the acid-dissociable group shown by the formula (1-3) include a methylcarbonate group, a p-nitrophenyl carbonate group, and a benzyl carbonate group.

Further examples of the acid-dissociable group represented by $R^3$ include groups shown by the following formulas.

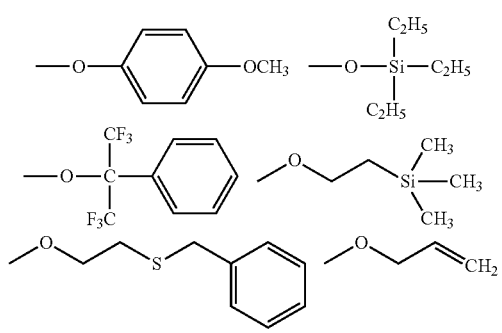

n is an integer from 1 to 6, preferably 1 or 2, and particularly preferably 1.

Examples of the alkyl group having 1 to 4 carbon atoms represented by each of $R^{4A}$, $R^{4B}$, and $R^{4C}$ include a methyl group, an ethyl group, an n-propyl group, an n-butyl group, and the like. Examples of the monovalent alicyclic hydrocarbon group having 4 to 20 carbon atoms represented by $R^{4A}$ or the divalent alicyclic hydrocarbon group having 4 to 20 carbon atoms formed by $R^{4B}$ and $R^{4C}$ together with the carbon atom that is bonded to $R^{4B}$ and $R^{4C}$ include the alicyclic hydrocarbon groups mentioned above in connection with $R^2$.

Examples of the group (second acid-dissociable group) represented by $-CR^{4A}R^{4B}R^{4C}$ in the formula (1) include branched alkyl groups (e.g., tert-butyl group and tert-amyl group); and alicyclic structure-containing groups shown by the following formulas. Among these, a tert-butyl group and a tert-amyl group are preferable from the viewpoint of sensitivity control.

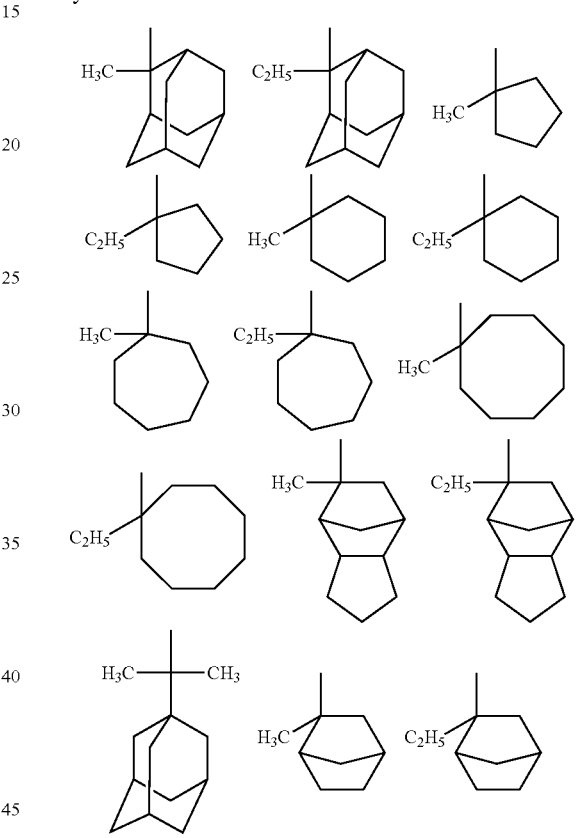

Preferable specific examples of the compound (A) include compounds shown by the following formulas (1-1a) to (1-1i). Note that $R^{4A}$, $R^{4B}$, and $R^{4C}$ in the formulas (1-1a) to (1-1i) are the same as defined above, and the group represented by $-CR^{4A}R^{4B}R^{4C}$ is preferably a tert-butyl group or a tert-amyl group.

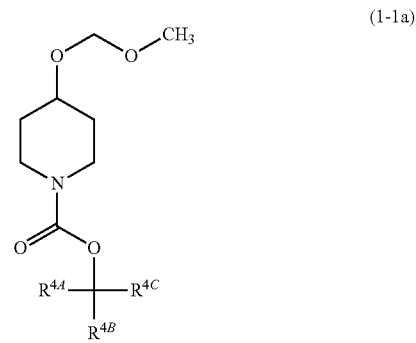

(1-1a)

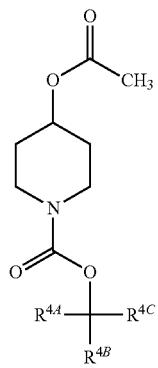
(1-1b)

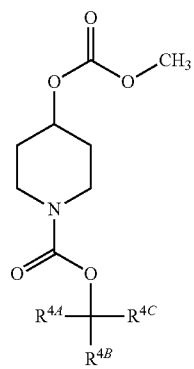
(1-1c)

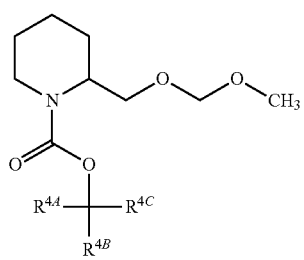
(1-1d)

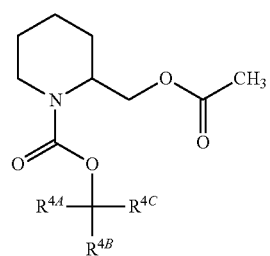
(1-1e)

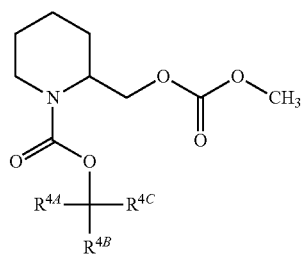
(1-1f)

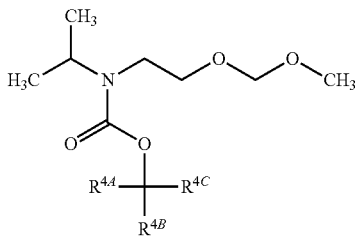
(1-1g)

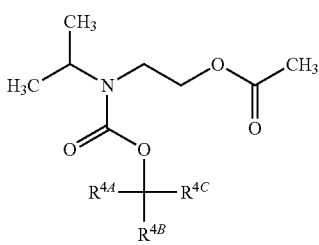
(1-1h)

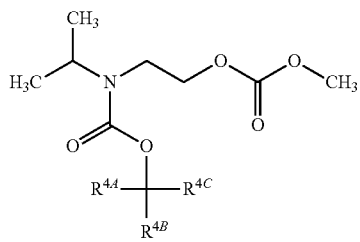
(1-1i)

The compound (A) may be synthesized by protecting the amine site of a hydroxyl group-containing amine compound by di-tert-butyl dicarbonate or like, and protecting the alcohol site of the resulting compound using methoxymethyl chloride or the like.

The compound (A) is a low-molecular-weight compound preferably having a molecular weight of 180 to 400.

The content of the compound (A) in the radiation-sensitive resin composition according to one embodiment of the invention is preferably 0.01 to 20 wt %, and particularly preferably 0.1 to 10 wt %, based on the amount of the resin (B).

The compound (A) may be used in combination with an additional nitrogen-containing compound such as a tertiary amine compound or a quaternary ammonium hydroxide compound.

Examples of the tertiary amine compound include tri(cyclo)alkylamines such as triethylamine, tri-n-propylamine, and tri-n-butylamine; aromatic amines such as aniline, N-methylaniline, and N,N-dimethylaniline; alkanolamines such as triethanolamine and N,N-di(hydroxyethyl)aniline; N,N,N',N'-tetramethylethylenediamine, N,N,N',N'-tetrakis(2-hydroxypropyl)ethylenediamine, 1,3-bis[1-(4-aminophenyl)-1-methylethyl]benzenetetramethylenediamine, bis(2-dimethylaminoethyl)ether, bis(2-diethylaminoethyl)ether, and the like.

Examples of the quaternary ammonium hydroxide compound include tetra-n-propylammonium hydroxide, tetra-n-butylammonium hydroxide, and the like.

The additional nitrogen-containing compound is preferably used in an amount of 50 wt % or less based on the total amount of the compound (A) and the additional nitrogen-containing compound.

Resin (B)

The resin (B) is protected by an acid-dissociable group, the resin (B) being insoluble or scarcely soluble in alkali, but becoming alkali-soluble upon dissociation of the acid-dissociable group. The expression "insoluble or scarcely soluble in alkali" means that a film that is formed only of the resin (B) has a thickness equal to or more than 50% of the initial thickness when developed under alkaline development conditions employed when forming a resist pattern using a resist film that is formed of the radiation-sensitive resin composition according to one embodiment of the invention.

The resin (B) preferably includes a repeating unit (2) shown by the formula (2) as a unit that includes the acid-dissociable group.

Examples of the alkyl group having 1 to 4 carbon atoms represented by each of $R^{11A}$, $R^{11B}$, and $R^{11C}$ in the formula (2) include a methyl group, an ethyl group, an n-propyl group, an n-butyl group, and the like. Examples of the monovalent alicyclic hydrocarbon group having 4 to 20 carbon atoms represented by $R^{11A}$ or the divalent alicyclic hydrocarbon group having 4 to 20 carbon atoms formed by $R^{11B}$ and $R^{11C}$ together with the carbon atom that is bonded to $R^{11B}$ and $R^{11C}$ include the alicyclic hydrocarbon groups mentioned above in connection with $R^2$ and $R^5$.

Examples of the group represented by $-CR^{11A}R^{11B}R^{11C}$ in the formula (2) include the groups mentioned above in connection with the group represented by $-CR^{4A}R^{4B}R^{4C}$ included in the compound (A).

It is preferable that the repeating unit (2) be any of repeating units shown by the following formulas (2-1) to (2-18). Among these, the repeating units shown by the formulas (2-3), (2-4), (2-9), (2-3), (2-12), and (2-13) are particularly preferable. These repeating units may be used either individually or in combination.

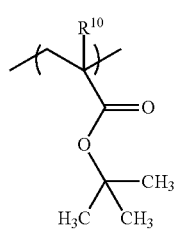

(2-1)

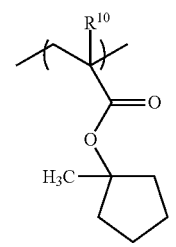

(2-2)

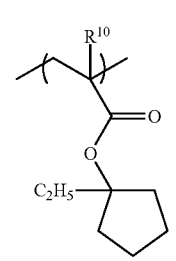
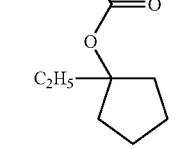

(2-3)

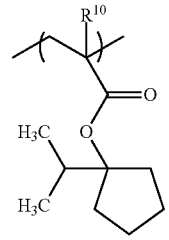

(2-4)

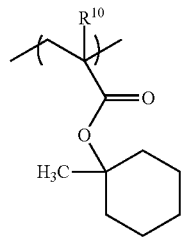

(2-5)

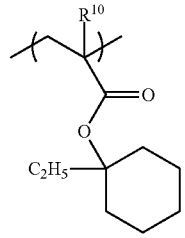

(2-6)

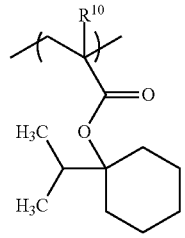

(2-7)

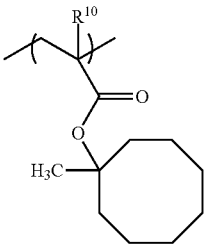

(2-8)

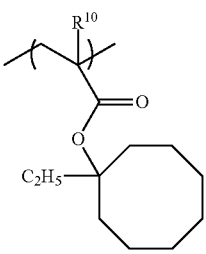

(2-9)

(2-10) 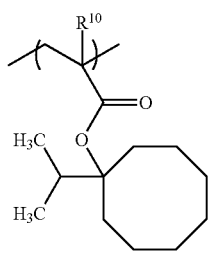

(2-11) 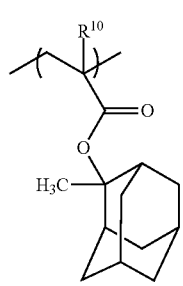

(2-12) 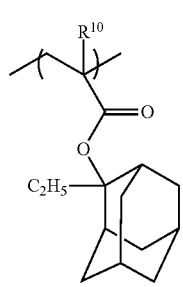

(2-13) 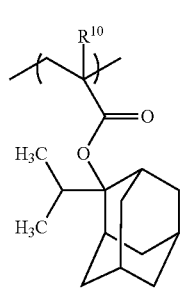

(2-14) 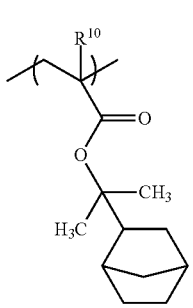

(2-15) 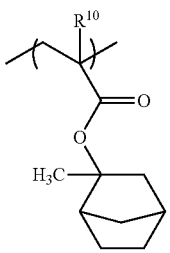

(2-16) 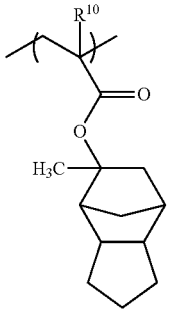

(2-17) 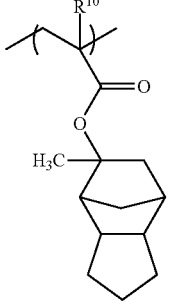

(2-18) 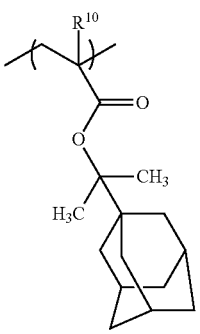

wherein $R^{10}$ is the same as defined in connection with the formula (2).

The content of the repeating unit (2) in the resin (B) is preferably 5 to 80 mol %, more preferably 10 to 80 mol %, and particularly preferably 20 to 70 mol %, based on the total amount of the repeating units that form the resin (B). If the content of the repeating unit (2) is more than 80 mol %, the adhesion of the resulting resist film may decrease, so that pattern collapse or pattern separation may occur.

The resin (B) preferably includes a repeating unit that is shown by the following formula and includes a lactone skeleton or a cyclic carbonate skeleton (hereinafter may be referred to as "repeating unit (3)").

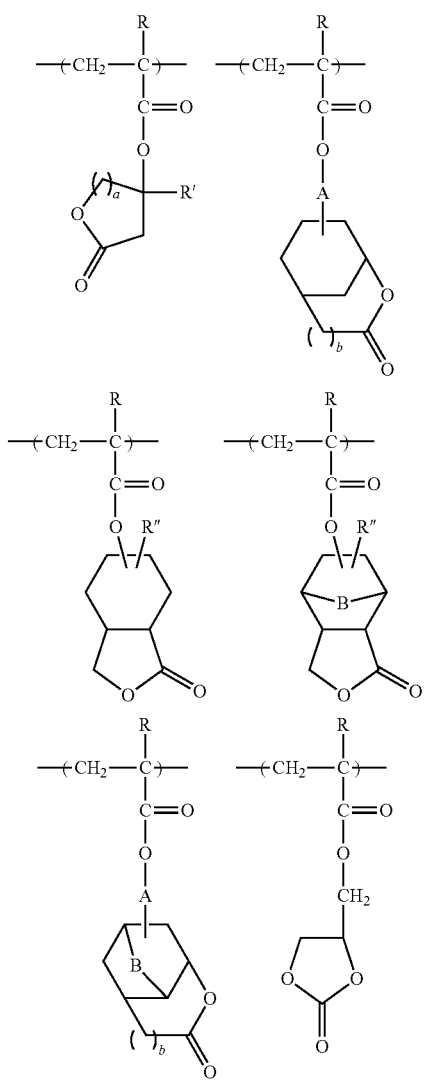

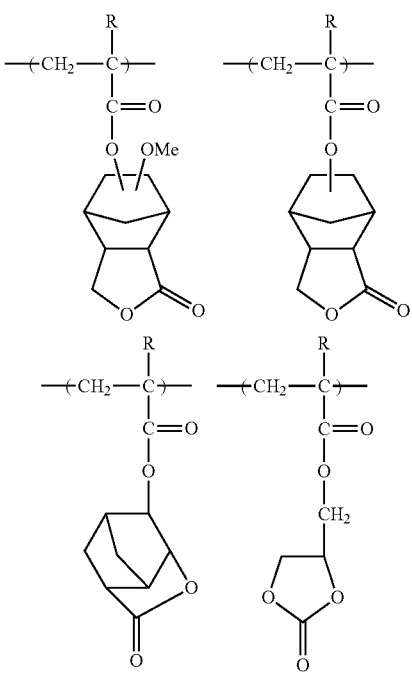

The content of the repeating unit (3) in the resin (B) is preferably 0 to 70 mol %, and more preferably 0 to 60 mol %, based on the total amount of the repeating units that form the resin (B). If the content of the repeating unit (3) is within the above range, the resulting resist exhibits improved developability, low defectivity, low LWR, low PEB temperature dependence, etc. If the content of the repeating unit (3) is more than 70 mol %, the resulting resist may show a decrease in resolution and an increase in LWR.

The resin (B) may include any of functional group-containing repeating units shown by the following formulas.

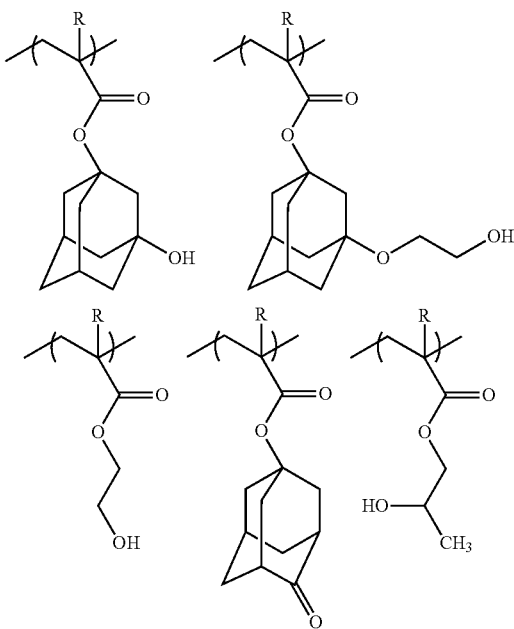

wherein each of R and R' represents one of a hydrogen atom and a methyl group, R" represents a hydrogen atom or a methoxy group, A represents a single bond or a methylene group, B represents a methylene group or an oxygen atom, and a and b are 0 or 1.

Repeating units shown by the following formulas are particularly preferable as the repeating unit (3).

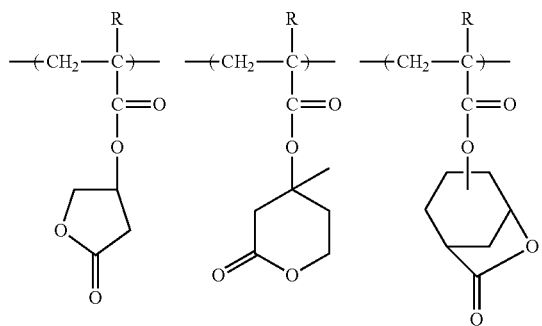

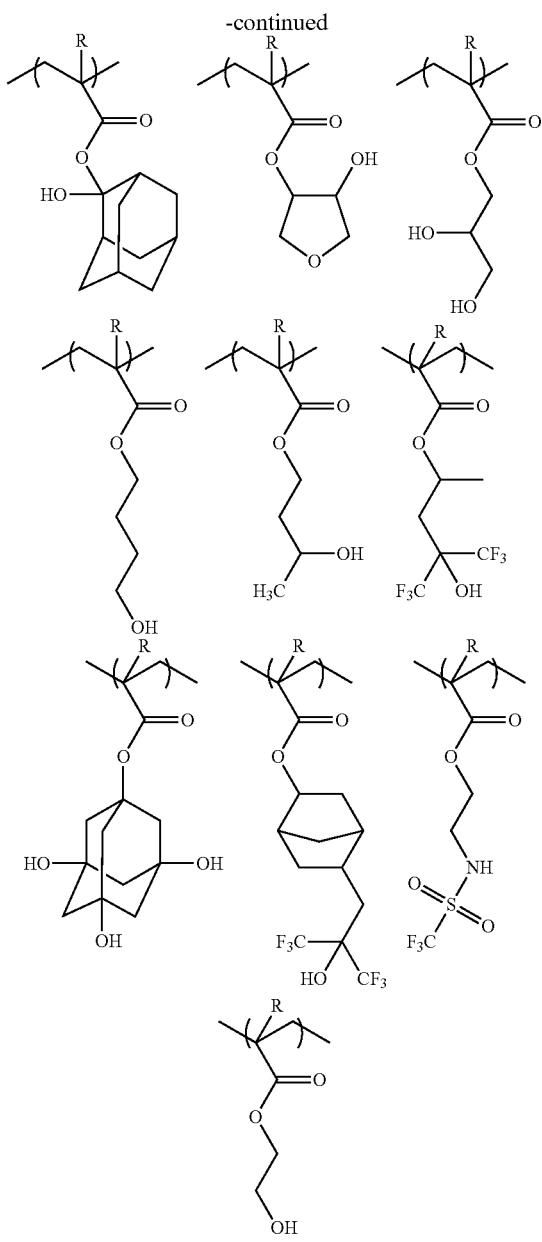

The resin (B) may include an alkyl (meth)acrylate such as methyl (meth)acrylate, ethyl (meth)acrylate, butyl (meth)acrylate, lauryl (meth)acrylate, cyclohexyl (meth)acrylate, bicyclo[2.2.1]heptyl (meth)acrylate, cyclohexyl (meth)acrylate, bicyclo[4.4.0]decanyl (meth)acrylate, bicyclo[2.2.2]octyl (meth)acrylate, tricyclo[5.2.1.0$^{2,6}$]decanyl (meth)acrylate, adamantyl (meth)acrylate, and tricyclo[3.3.1.1$^{3,7}$]decanyl (meth)acrylate.

The resin (B) may be synthesized by radical polymerization or the like. For example, the resin (B) is preferably synthesized by (1) polymerizing a monomer while adding a solution containing a monomer and a radical initiator dropwise to a solution containing a reaction solvent or a monomer, (2) polymerizing a monomer while adding a solution containing a monomer and a solution containing a radical initiator dropwise to a solution containing a reaction solvent or a monomer, (3) polymerizing a monomer while adding a plurality of solutions containing different types of monomers and a solution containing a radical initiator dropwise to a solution containing a reaction solvent or a monomer, or the like.

The content of monomers in the monomer solution that is added dropwise to another monomer solution is preferably 30 mol % or more, more preferably 50 mol % or more, and particularly preferably 70 mol % or more, based on the total amount of monomers used for polymerization.

The reaction temperature may be appropriately determined depending on the type of initiator. The reaction temperature is normally 30 to 180° C., preferably 40 to 160° C., and more preferably 50 to 140° C. The addition time differs depending on the reaction temperature, the type of initiator, the type of monomer, and the like, but is normally 30 minutes to 8 hours, preferably 45 minutes to 6 hours, and more preferably 1 to 5 hours. The total reaction time including the addition time also differs depending on the reaction conditions, but is normally 30 minutes to 8 hours, preferably 45 minutes to 7 hours, and more preferably 1 to 6 hours.

Examples of the radical initiator used for polymerization include 2,2'-azobis(4-methoxy-2,4-dimethylvaleronitrile), 2,2'-azobis(2-cyclopropylpropionitrile), 2,2'-azobis(2,4-dimethylvaleronitrile), and the like. These radical initiators may be used either individually or in combination.

A solvent that is other than a solvent that hinders polymerization (e.g., nitrobenzene having a polymerization inhibiting effect or a mercapto compound having a chain transfer effect) and dissolves the monomers may be used as the polymerization solvent. Examples of such a solvent include an alcohol solvent, an ether solvent, a ketone solvent, an amide solvent, an ester-lactone solvent, a nitrile solvent, a mixture thereof, and the like. These solvents may be used either individually or in combination.

The resin obtained by polymerization is preferably collected by re-precipitation. Specifically, the polymer solution is poured into a re-precipitation solvent after completion of polymerization to collect the target resin as a powder. The above polymerization solvents may be used as the re-precipitation solvent either individually or in combination. The resin may be collected by removing low-molecular-weight components (e.g., monomer and oligomer) by a separatory operation. Specifically, the polymer solution is appropriately concentrated after completion of polymerization. A two-liquid solvent system (e.g., methanol/heptane) is added to the polymer solution to remove low-molecular-weight components from the resin solution. The solvent is appropriately replaced with a necessary solvent system (e.g., propylene glycol monomethyl ether) to collect the target resin as a solution.

The polystyrene-reduced weight average molecular weight (Mw) of the resin (B) determined by gel permeation chromatography (GPC) is not particularly limited, but is preferably 1000 to 100,000, preferably 1000 to 30,000, and particularly preferably 1000 to 20,000. If the Mw of the resin (B) is less than 1000, the heat resistance of the resulting resist may decrease. If the Mw of the resin (B) is more than 100,000, the developability of the resulting resist may decrease.

The ratio (Mw/Mn) of the Mw to the polystyrene-reduced number average molecular weight (Mn) of the resin (B) determined by gel permeation chromatography (GPC) is normally 1.0 to 5.0, preferably 1.0 to 3.0, and more preferably 1.0 to 2.0.

The radiation-sensitive resin composition according to one embodiment of the invention may include only one type of resin (B), or may include two or more types of resins (B).

Acid Generator (C)

Examples of the acid generator (C) included in the radiation-sensitive resin composition according to one embodiment of the invention include onium salts (e.g., sulfonium salts and iodonium salts), organic halogen compounds, and sulfone compounds (e.g., disulfones and diazomethanesulfones).

Preferable specific examples of the acid generator (C) include triphenylsulfonium salt compounds such as triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, and triphenylsulfonium camphorsulfonate; 4-cyclohexylphenyldiphenylsulfonium salt compounds such as 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, and 4-cyclohexylphenyldiphenylsulfonium camphorsulfonate; 4-methanesulfonylphenyldiphenylsulfonium salt compounds such as 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, and 4-methanesulfonylphenyldiphenylsulfonium camphorsulfonate; diphenylodonium salt compounds such as diphenylodonium trifluoromethanesulfonate, diphenylodonium nonafluoro-n-butanesulfonate, diphenylodonium perfluoro-n-octanesulfonate, diphenylodonium 2-bicyclo[2.2.1]hept-2-yl-1,1,2,2-tetrafluoroethanesulfonate, and diphenylodonium camphorsulfonate; bis(4-t-butylphenyl)iodonium salt compounds such as bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, and bis(4-t-butylphenyl)iodonium camphorsulfonate; 1-(4-n-butoxynaphthalen-1-yl)tetrahydrothiophenium salt compounds such as 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl)tetrahydrothiophenium 2-bicyclo[2.2.1]hept-2-yl-1,1,2,2-tetrafluoroethanesulfonate, and 1-(4-n-butoxynaphthalen-1-yl)tetrahydrothiophenium camphorsulfonate; 1-(6-n-butoxynaphthalen-2-yl)tetrahydrothiophenium salt compounds such as 1-(6-n-butoxynaphthalen-2-yl)tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl)tetrahydrothiophenium perfluoro-n-octanesulfonate, 1-(6-n-butoxynaphthalen-2-yl)tetrahydrothiophenium 2-bicyclo[2.2.1]hept-2-yl-1,1,2,2-tetrafluoroethanesulfonate, and 1-(6-n-butoxynaphthalen-2-yl)tetrahydrothiophenium camphorsulfonate; 1-(3,5-dimethyl-4-hydroxyphenyl)tetrahydrothiophenium salt compounds such as 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1,1,2,2-tetrafluoroethanesulfonate, and 1-(3,5-dimethyl-4-hydroxyphenyl)tetrahydrothiophenium camphorsulfonate; bicyclo[2.2.1]hept-5-ene-2,3-dicarboxyimide compounds such as N-(trifluoromethanesulfonyloxy)bicyclo[2.2.1]hept-5-ene-2,3-dicarboxyimide, N-(nonafluoro-n-butanesulfonyloxy)bicyclo[2.2.1]hept-5-ene-2,3-dicarboxyimide, N-(perfluoro-n-octanesulfonyloxy)bicyclo[2.2.1]hept-5-ene-2,3-dicarboxyimide, N-(2-bicyclo[2.2.1]hept-2-yl-1,1,2,2-tetrafluoroethanesulfonyloxy) bicyclo[2.2.1]hept-5-ene-2,3-dicarboxyimide, N-(2-(3-tetracyclo[4.4.0.1$^{2,5}$0.1$^{7,10}$]dodecanyl)-1,1-difluoroethanesulfonyloxy) bicyclo[2.2.1]hept-5-ene-2,3-dicarboxyimide, and N-(camphorsulfonyloxy)bicyclo[2.2.1]hept-5-ene-2,3-dicarboxyimide; and the like.

These acid generators (C) may be used either individually or in combination. The content of the acid generator (C) is preferably 0.1 to 30 parts by mass, and more preferably 0.1 to 20 parts by mass, based on 100 parts by mass of the resin (B), from the viewpoint of ensuring that the resulting resist exhibits excellent sensitivity and developability. If the content of the acid generator (C) is less than 0.1 parts by mass, the sensitivity and the developability of the resulting resist may decrease. If the content of the acid generator (C) is more than 30 parts by mass, a rectangular resist pattern may not be obtained due to a decrease in transparency to radiation.

Solvent

The radiation-sensitive resin composition according to one embodiment of the invention normally includes a solvent. Any solvent that can dissolve at least the compound (A), the resin (B), the acid generator (C), and optionally an additive (E) may be appropriately used.

Examples of such a solvent include an alcohol solvent, an ether solvent, a ketone solvent, an amide solvent, an ester-lactone solvent, a nitrile solvent, a mixture thereof, and the like.

Among these, it is preferable to use a propylene glycol monoalkyl ether acetate (particularly propylene glycol monomethyl ether acetate). It is also preferable to use a ketone, an alkyl 2-hydroxypropionate, an alkyl 3-alkoxypropionate, γ-butyrolactone, or the like. These solvents may be used either individually or in combination.

Other Components

The radiation-sensitive resin composition according to one embodiment of the invention may optionally include the additive (E) such as a fluorine-containing resin, an alicyclic skeleton-containing resin, a surfactant, and a sensitizer. The content of each additive may be appropriately determined depending on the application.

The fluorine-containing resin provides water repellency to the surface of the resulting resist film during liquid immersion lithography. The fluorine-containing resin suppresses elution of components from the resist film into an immersion liquid, or suppresses defects (e.g., watermark defect) that may occur due to liquid immersion lithography even if high-speed scan is performed.

The structure of the fluorine-containing resin is not particularly limited. Examples of the fluorine-containing resin include (1) a fluorine-containing resin that is insoluble in a developer, but becomes alkali-soluble due to an acid, (2) a fluorine-containing resin that is soluble in a developer, and becomes more alkali-soluble due to an acid, (3) a fluorine-containing resin that is insoluble in a developer, and becomes alkali-soluble due to alkali, (4) a fluorine-containing resin that is soluble in a developer, and becomes more alkali-soluble due to alkali, and the like.

Examples of the fluorine-containing resin include a resin (polymer) that includes at least one repeating unit selected from a repeating unit (4) and a fluorine-containing repeating unit. The fluorine-containing resin is preferably a polymer that further includes at least one repeating unit selected from the group consisting of repeating units (1) to (3), (5), and (6).

Examples of the fluorine-containing repeating unit include trifluoromethyl (meth)acrylate, 2,2,2-trifluoroethyl (meth) acrylate, perfluoroethyl (meth)acrylate, and the like.

The fluorine-containing resin is preferably a copolymer that includes the fluorine-containing repeating unit and the acid-dissociable group-containing repeating unit (3) mentioned above as the repeating unit that forms the resin (B), for example. These fluorine-containing resins may be used either individually or in combination.

The alicyclic skeleton-containing compound improves the dry etching resistance, the pattern shape, adhesion to a substrate, etc.

Examples of the alicyclic skeleton-containing compound include adamantane derivatives such as 1-adamantanecarboxylic acid, 2-adamantanone, and t-butyl 1-adamantanecarboxylate; deoxycholates such as t-butyl deoxycholate, t-butoxycarbonylmethyl deoxycholate, and 2-ethoxyethyl deoxycholate; lithocholates such as t-butyl lithocholate, t-butoxycarbonylmethyl lithocholate, and 2-ethoxyethyl lithocholate; alkyl carboxylates such as dimethyl adipate, diethyl adipate, and dipropyl adipate; 3-[2-hydroxy-2,2-bis(trifluoromethyl)ethyl]tetracyclo[4.4.0.1$^{2,5}$0.1$^{7,10}$]dodecane, 2-hydroxy-9-methoxycarbonyl-5-oxo-4-oxa-tricyclo[4.2.1.0$^{3,7}$]nonane, and the like. These alicyclic skeleton-containing compounds may be used either individually or in combination.

The surfactant improves applicability, striation, developability, etc. Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate, and polyethylene glycol distearate, commercially available products such as KP341 (manufactured by Shin-Etsu Chemical Co., Ltd.), Polyflow No. 75, Polyflow No. 95 (manufactured by Kyoeisha Chemical Co., Ltd.), EFTOP EF301, EFTOP EF303, EFTOP EF352 (manufactured by JEMCO, Inc.), MEGAFAC F171, MEGAFAC F173 (manufactured by Dainippon Ink and Chemicals, Inc.), Fluorad FC430, Fluorad FC431 (manufactured by Sumitomo 3M Ltd.), Asahi Guard AG710, Surflon S-382, Surflon SC-101, Surflon SC-102, Surflon SC-103, Surflon SC-104, Surflon SC-105, Surflon SC-106 (manufactured by Asahi Glass Co., Ltd.), and the like. These surfactants may be used either individually or in combination.

The sensitizer absorbs the energy of radiation, and transmits the energy to the acid generator (C) so that the amount of acid generated increases. The sensitizer thus improves the apparent sensitivity of the radiation-sensitive resin composition.

Examples of the sensitizer include carbazoles, acetophenones, benzophenones, naphthalenes, phenols, biacetyl, eosine, rose bengal, pyrenes, anthracenes, phenothiazines, and the like. These sensitizers may be used either individually or in combination.

A dye, a pigment, an adhesion improver, or the like may also be used as the additive (E). For example, a dye or a pigment visualizes the latent image in the exposed area so that the effect of halation during exposure can be reduced. An adhesion improver improves adhesion to a substrate. Examples of further additives include an alkali-soluble resin, a low-molecular-weight alkali-solubility controller that includes an acid-dissociable protecting group, a halation inhibitor, a preservation stabilizer, an anti-foaming agent, and the like.

The additives (E) may be used either individually or in combination.

Formation of Photoresist Pattern

The radiation-sensitive resin composition according to one embodiment of the present invention is useful as a chemically-amplified resist. When using the radiation-sensitive resin composition as a chemically-amplified resist, the acid-dissociable group of the resin component (mainly the compound (A)) dissociates due to an acid generated by the acid generator upon exposure to produce a carboxyl group. As a result, the solubility of the exposed area of the resist in an alkaline developer increases. Therefore, the exposed area is dissolved and removed by the alkaline developer to obtain a positive-tone photoresist pattern.

Photoresist Pattern-Forming Method

A photoresist pattern is normally formed as follows, for example. Specifically, a photoresist film is formed on a substrate using the radiation-sensitive resin composition (step (1)). The photoresist film is exposed to radiation via a mask having a given pattern (optionally via an immersion medium (step (2)). After heating the substrate (exposed photoresist film) (step (3)), the exposed photoresist film is developed (step (4)) to form a photoresist pattern.

In the step (1), the radiation-sensitive resin composition or a composition solution obtained by dissolving the radiation-sensitive resin composition in a solvent is applied to the substrate (e.g., a silicon wafer or a wafer coated with silicon dioxide and an antireflective film) by an appropriate application method (e.g., rotational coating, cast coating, or roll coating) to form a photoresist film. Specifically, the resin composition solution is applied to the substrate so that the resulting resist film has a given thickness, and is pre-baked (PB) to volatilize the solvent from the film to obtain a resist film.

In the step (2), the photoresist film formed by the step (1) is exposed to radiation (optionally via an immersion medium such as water). In this case, radiation is applied via a mask having a given pattern. Radiation used for exposure is appropriately selected from visible rays, ultraviolet rays, deep ultraviolet rays, X-rays, charged particle rays, and the like, depending on the line width of the target pattern. It is preferable to use deep ultraviolet rays such as ArF excimer laser light (wavelength: 193 nm) or KrF excimer laser light (wavelength: 248 nm). It is particularly preferable to use ArF excimer laser light.

In the step (3) (post-exposure bake (PEB)), the polymer is deprotected by an acid generated by the acid generator in the area of the photoresist film that has been exposed by the step (2). A difference in solubility in an alkaline developer occurs between the exposed area and the unexposed area. The PEB temperature is appropriately selected within the range from 50 to 180° C.

In the step (4), the exposed photoresist film is developed using a developer to form a given photoresist pattern. After development, the photoresist film is normally washed with water, and dried. An alkaline aqueous solution prepared by dissolving at least one alkaline compound (e.g., sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene, or 1,5-diazabicyclo-[4.3.0]-5-nonene) in water is preferably used as the developer.

When employing liquid immersion lithography, a protective film that is insoluble in the immersion liquid may be formed on the resist film before the step (2) so that the immersion liquid does not directly come in contact with the resist film. A solvent removal-type protective film that is removed by a solvent prior to the step (4) (see Japanese Patent Application Publication (KOKAI) No. 2006-227632, for example), or a developer removal-type protective film that is removed during development in the step (4) (see WO2005/069076 and WO2006/035790, for example) may be used as the protective film. It is preferable to use the developer removal-type protective film from the viewpoint of throughput.

EXAMPLES

The embodiment of the invention is further described below by way of examples. Note that the invention is not limited to the following examples. In the examples, the unit "parts" refers to "parts by mass" unless otherwise indicated. In the examples and comparative examples, the following measurement and evaluation methods were employed.

Polystyrene-Reduced Weight Average Molecular Weight (Mw)

The polystyrene-reduced weight average molecular weight (Mw) was measured by gel permeation chromatography (GPC) using GPC columns (manufactured by Tosoh Corp., G2000HXL×2, G3000HXL×1, G4000HXL×1) at a flow rate of 1.0 ml/min and a column temperature of 40° C. (eluant: tetrahydrofuran, standard: monodisperse polystyrene).

Polystyrene-Reduced Number Average Molecular Weight (Mn)

The polystyrene-reduced number average molecular weight (Mn) was measured by gel permeation chromatography (GPC) using GPC columns (manufactured by Tosoh Corp., G2000HXL×2, G3000HXL×1, G4000HXL×1) at a flow rate of 1.0 ml/min and a column temperature of 40° C. (eluant: tetrahydrofuran, standard: monodisperse polystyrene).

$^{13}$C-NMR Analysis

Each polymer was subjected to $^{13}$C-NMR analysis using a spectrometer ("JNM-ECX400" manufactured by JEOL Ltd.).

Sensitivity (mJ/cm$^2$)

An underlayer anti-reflective film having a thickness of 77 nm was formed on the surface of an 8-inch silicon wafer (substrate) using a material "ARC29A" (manufactured by Nissan Chemical Industries, Ltd.). The radiation-sensitive resin composition of each example and comparative example was spin-coated onto the surface of the substrate, and soft-baked (SB) at 100° C. for 60 seconds on a hot plate to form a resist film having a thickness of 100 nm.

The resist film was exposed via a mask pattern using a full-field projection aligner ("S306C" manufactured by Nikon Corp., NA: 0.78). After subjecting the resist film to PEB at 100° C. for 60 seconds, the resist film was developed at 25° C. for 30 seconds using a 2.38 mass % tetramethylammonium hydroxide aqueous solution (hereinafter referred to as "TMAH aqueous solution"), washed with water, and dried to obtain a positive-tone resist pattern.

An optimum dose (mJ/cm$^2$) at which a 1:1 line-and-space (1L/1S) pattern having a line width of 90 nm was formed via a 1:1 line-and-space mask having a line width of 90 nm was taken as sensitivity. The measurement was performed using a scanning electron microscope ("S9260" manufactured by Hitachi High-Technologies Corporation).

Exposure Latitude (EL)

The ratio of the dose range in which the pattern dimension resolved via a 90 nm 1L/1S mask pattern was within ±10% of the mask design dimension to the optimum dose was taken as exposure latitude. A case where the exposure latitude was 13% or more was evaluated as "Good", and a case where the exposure latitude was less than 13% was evaluated as "Bad". The pattern dimension was measured using a scanning electron microscope ("S9260" manufactured by Hitachi High-Technologies Corporation).

MEEF

The dimension of a pattern resolved at the optimum dose using each mask (85.0 nmL/170 nmP, 90.0 nmL/180 nmP, and 95.0 nmL/190 nmP) was measured using a scanning electron microscope ("S9260" manufactured by Hitachi High-Technologies Corporation). The mask size (horizontal axis) and the line width (vertical axis) were plotted on a graph, and the slope of the graph was determined by a least-square method. The slope thus determined was taken as MEEF. A case where the MEEF was 1.3 or more was evaluated as "Good", and a case where the MEEF was less than 1.3 was evaluated as "Bad".

Example 1

10 ml of a tetrahydrofuran (THF) solution of 1.37 g (11 mmol) of 2-methoxyethoxymethyl chloride was added dropwise to 10 ml of a THF solution of 2.01 g (10 mmol) of N-t-butoxycarbonyl-4-hydroxypiperidine (manufactured by Aldrich) and 2.58 g (20 mmol) of diisopropylethylamine at 0° C. in a nitrogen atmosphere. After the addition, the reaction solution was allowed to reach room temperature, and stirred for one hour. After confirming disappearance of the raw materials by thin-layer chromatography (TLC), the reaction solution was cooled to 0° C. The reaction was then terminated by adding water. The reaction solution was subjected to an extraction operation three times using water and ethyl acetate. The resulting organic layer was washed once with a saturated ammonium chloride solution, washed once with water, washed once with a saturated sodium chloride aqueous solution, and dried over anhydrous sodium sulfate. After evaporating the solvent under reduced pressure, the product was purified by column chromatography to obtain 1.7 g of N-t-butoxycarbonyl-4-[(2-methoxyethoxy)methoxy]piperidine as a colorless liquid (hereinafter referred to as "compound (A-1)") (yield: 60%).

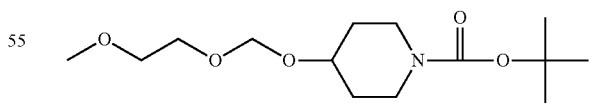

(A-1)

Synthesis of Resin (B)

In the synthesis example, a resin (B-1) was synthesized using the following monomers (M-1) to (M-3).

(M-1): 1-methylcyclopentyl methacrylate (M-2): 1-ethyladamantyl methacrylate (M-3): 4-oxa-5-oxotricyclo[4.2.1.0$^{3,7}$]nonan-2-yl methacrylate

Synthesis Example 1

Resin (B-1)

A monomer solution was prepared by dissolving 14.20 g (35 mol %) of the monomer (M-1), 8.99 g (15 mol %) of the monomer (M-2), and 26.81 g (50 mol %) of the monomer (M-3) in 100 g of 2-butanone, and adding 2.78 g (5 mol %) of dimethyl 2,2'-azobis(2-methylpropionate) (initiator) to the solution.

A 500 ml three-necked flask equipped with a thermometer and a dropping funnel was charged with 50 g of 2-butanone, and purged with nitrogen for 30 minutes. The inside of the flask was then heated to 80° C. with stirring using a magnetic stirrer. The monomer solution was added dropwise to the flask using the dropping funnel over three hours. The monomers were polymerized for six hours from the start of the addition of the monomer solution. After completion of polymerization, the polymer solution was cooled with water to 30° C. or less. The polymer solution was then added to 1000 g of hexane, and a precipitated white powder was collected by filtration. The white powder thus collected was dissolved in 200 g of 2-butanone. The solution was added to 1000 g of hexane, and a precipitated white powder was collected by filtration. The same operation was then repeated once. The white powder thus collected was dried at 50° C. for 17 hours to obtain a white powdery copolymer (38 g, yield: 75%). This copolymer is referred to as "resin (B-1)".

The copolymer had an Mw of 6520 and an Mw/Mn ratio of 1.61. The ratio of repeating units derived from the monomers (M-1), (M-2), and (M-3) determined by $^{13}$C-NMR analysis was 35.5:15.3:49.2 (mol %).

Preparation of Radiation-Sensitive Resin Composition

Table 1 shows the compositions of the radiation-sensitive resin compositions prepared in Example 2 and the Comparative Example. The low-molecular-weight compound (A) and components (acid generator (C) and solvent (D)) of the radiation-sensitive composition other than the resin (B-1) synthesized in the synthesis example are given below.

Other Amine Compound
(A-2): N-t-butoxycarbonyl-4-hydroxypiperidine
Acid Generator (C)
(C-1): triphenylsulfonium 2-bicyclo[2.2.1]hept-2-yl-1,1-difluoroethanesulfonate
Solvent (D)
(D-1): propylene glycol monomethyl ether acetate
(D-2): cyclohexanone
(D-3): γ-butyrolactone

TABLE 1

| | Low-molecular-weight compound (A) | Resin (B) | | Photoacid generator (C) | | Solvent (D) | |
|---|---|---|---|---|---|---|---|
| | Type | Parts by mass | Type | Type | Parts by mass | Type | Parts by mass |
| Example 2 | A-1 | 0.7 | B-1 | C-1 | 7.5 | D-1 | 1500 |
| | | | | | | D-2 | 650 |
| | | | | | | D-3 | 30 |
| Comparative Example | A-2 | 0.7 | B-1 | C-1 | 7.5 | D-1 | 1500 |
| | | | | | | D-2 | 650 |
| | | | | | | D-3 | 30 |

Example 2

0.7 parts by mass of the low-molecular-weight compound (A-1), 100 parts by mass of the resin (B-1) obtained in Synthesis Example 1, and 7.5 parts by mass of triphenylsulfonium 2-bicyclo[2.2.1]hept-2-yl-1,1-difluoroethanesulfonate (C-1) (acid generator (C)) were mixed. 1650 parts by mass of propylene glycol monomethyl ether acetate (D-1), 700 parts by mass of cyclohexanone (D-2), and 30 parts by mass of γ-butyrolactone (D-3) (solvent (D)) were added to the mixture to obtain a mixed solution. The resulting mixed solution was filtered through a filter having a pore size of 0.20 μm to obtain a radiation-sensitive resin composition.

Comparative Example

A radiation-sensitive resin composition was obtained in the same manner as in Example 2, except for changing the components as shown in Table 1.

Evaluation Methods

The sensitivity, EL, and MEEF of the radiation-sensitive resin compositions of Example 2 and the Comparative Example were evaluated using an ArF excimer laser as a light source. The evaluation results are shown in Table 2.

TABLE 2

| | SB (° C.) | PEB (° C.) | Sensitivity (mJ/cm$^2$) | EL | MEEF |
|---|---|---|---|---|---|
| Example 2 | 100 | 100 | 40.3 | 13.2 | 1.22 |
| Comparative Example | 100 | 100 | 42.6 | 11.9 | 1.42 |

The radiation-sensitive resin composition according to the embodiments of the invention may be suitably used as a lithography material when using a KrF excimer laser or an ArF excimer laser as a light source. The radiation-sensitive resin composition may also be used for liquid immersion lithography.

Obviously, numerous modifications and variations of the invention are possible in light of the above teachings. It is therefore to be understood that within the scope of the appended claims, the invention may be practiced otherwise than as specifically described herein.

What is claimed as new and desired to be secured by Letters Patent of the United States is:

1. A radiation-sensitive resin composition comprising:
   (A) a compound shown by a formula (1);
   (B) a resin protected by an acid-dissociable group and being insoluble or scarcely soluble in alkali, the resin becoming alkali-soluble upon dissociation of the acid-dissociable group; and
   (C) a photoacid generator, $$(R^3-O)_n-R^1 \diagdown N-\underset{\underset{O}{\|}}{C}-O \diagup R^{4A} \diagdown R^{4B} \diagup R^{4C} \qquad (1)$$

wherein
   $R^1$ represents a hydrocarbon group having 1 to 20 carbon atoms and $R^2$ represents a hydrogen atom or a monovalent hydrocarbon group having 1 to 20 carbon atoms, or
   $R^1$ and $R^2$ are such that $R^1$ and $R^2$ together with a nitrogen atom form a heterocyclic structure having 4 to 20 carbon atoms if $R^1$ and $R^2$ bond with each other via the nitrogen atom, wherein $R^3$ represents a monovalent acid-dissociable group, n is an integer from 1 to 6, wherein each of $R^{4A}$, $R^{4B}$, and $R^{4C}$ represents one of an alkyl group having 1 to 4 carbon atoms and a monovalent alicyclic hydrocarbon group having 4 to 20 carbon atoms, or $R^{4A}$ represents one of an alkyl group having 1 to 4 carbon atoms and a monovalent alicyclic hydrocarbon group having 4 to 20 carbon atoms and $R^{4B}$ and $R^{4C}$ are such that $R^{4B}$ and $R^{4C}$ together with a carbon atom form a divalent alicyclic hydrocarbon group having 4 to 20 carbon atoms if $R^{4B}$ and $R^{4C}$ bond with each other via the carbon atom, and wherein $R^3$ in the formula (1) comprises a group shown by formula (I-1),

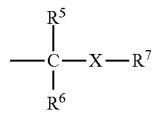
(1-1)

wherein

X represents an oxygen atom or a sulfur atom, each of $R^5$ and $R^6$ represents one of a hydrogen atom, an alkyl group having 1 to 20 carbon atoms, and an alkoxy group having 1 to 20 carbon atoms, and $R^7$ represents one of an alkyl group having 1 to 20 carbon atoms, an alkoxyalkyl group having 2 to 20 carbon atoms, an alicyclic hydrocarbon hydrocarbon group having 3 to 20 carbon atoms, an aryl group having 6 to 18 carbon atoms, and an aralkyl group having 7 to 19 carbon atoms.

2. The radiation-sensitive resin composition according to claim 1, wherein the group represented by —$CR^{4A}R^{4B}R^{4C}$ in the formula (1) comprises one of a tert-butyl group and a tert-amyl group.

3. The radiation-sensitive resin composition according to claim 1, wherein the resin (B) comprises a repeating unit shown by a formula (2),

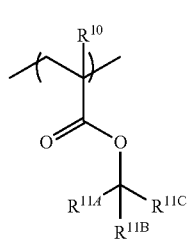
(2)

wherein $R^{10}$ represents a hydrogen atom or a methyl group, and wherein each of $R^{11A}$, $R^{11B}$, and $R^{11C}$ represents one of a linear or branched alkyl group having 1 to 4 carbon atoms and an alicyclic hydrocarbon group having 4 to 20 carbon atoms, or $R^{11A}$ represents one of a linear or branched alkyl group having 1 to 4 carbon atoms and an alicyclic hydrocarbon group having 4 to 20 carbon atoms and $R^{11B}$ and $R^{11C}$ are such that $R^{11B}$ and $R^{11C}$ together with a carbon atom form an alicyclic hydrocarbon group having 4 to 20 carbon atoms if $R^{11B}$ and $R^{11C}$ bond with each other via the carbon atom.

4. The radiation-sensitive resin composition according to claim 1, wherein n=1.

5. A compound shown by a formula (1),

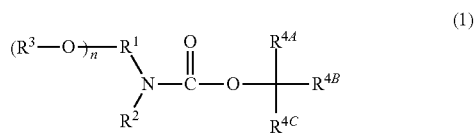
(1)

wherein $R^1$ represents a divalent hydrocarbon group having 1 to 20 carbon atoms and $R^2$ represents a hydrogen atom or a monovalent hydrocarbon group having 1 to 20 carbon atoms, or $R^1$ and $R^2$ are such that $R^1$ and $R^2$ together with a nitrogen atom form a heterocyclic structure having 4 to 20 carbon atoms if $R^1$ and $R^2$ bond with each other via the nitrogen atom, wherein $R^3$ represents a monovalent acid-dissociable group, n is an integer from 1 to 6, wherein each of $R^{4A}$, $R^{4B}$, and $R^{4C}$ represents one of an alkyl group having 1 to 4 carbon atoms and a monovalent alicyclic hydrocarbon group having 4 to 20 carbon atoms, or $R^{4A}$ represents one of an alkyl group having 1 to 4 carbon atoms and a monovalent alicyclic hydrocarbon group having 4 to 20 carbon atoms and $R^{4B}$ and $R^{4C}$ are such that $R^{4B}$ and $R^{4C}$ together with a carbon atom form a divalent alicyclic hydrocarbon group having 4 to 20 carbon atoms if $R^{4B}$ and $R^{4C}$ bond with each other via the carbon atom, and wherein $R^3$ in the formula (1) comprises a group shown by formula (I-1),

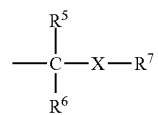
(1-1)

wherein

X represents an oxygen atom or a sulfur atom, each of $R^5$ and $R^6$ represents one of a hydrogen atom, an alkyl group having 1 to 20 carbon atoms, and an alkoxy group having 1 to 20 carbon atoms, and $R^7$ represents one of an alkyl group having 1 to 20 carbon atoms, an alkoxyalkyl group having 2 to 20 carbon atoms, an alicyclic hydrocarbon hydrocarbon group having 3 to 20 carbon atoms, an aryl group having 6 to 18 carbon atoms, and an aralkyl group having 7 to 19 carbon atoms.

6. The compound according to claim 5, wherein n=1.

7. A radiation-sensitive resin composition comprising:

(A) a compound shown by a formula (1);

(B) a resin protected by an acid-dissociable group and being insoluble or scarcely soluble in alkali, the resin becoming alkali-soluble upon dissociation of the acid-dissociable group; and (C) a photoacid generator,

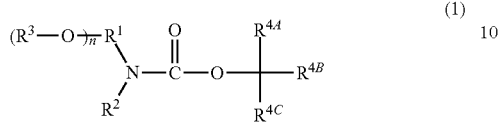

wherein
- $R^1$ represents a hydrocarbon group having 1 to 20 carbon atoms and $R^2$ represents a hydrogen atom or a monovalent hydrocarbon group having 1 to 20 carbon atoms, or
- $R^1$ and $R^2$ are such that $R^1$ and $R^2$ together with a nitrogen atom form a heterocyclic structure having 4 to 20 carbon atoms if $R^1$ and $R^2$ bond with each other via the nitrogen atom, wherein $R^3$ represents a monovalent acid-dissociable group, n is an integer from 1 to 6, wherein
- each of $R^{4A}$, $R^{4B}$, and $R^{4C}$ represents one of an alkyl group having 1 to 4 carbon atoms and a monovalent alicyclic hydrocarbon group having 4 to 20 carbon atoms, or
- $R^{4A}$ represents one of an alkyl group having 1 to 4 carbon atoms and a monovalent alicyclic hydrocarbon group having 4 to 20 carbon atoms and $R^{4B}$ and $R^{4C}$ are such that $R^{4B}$ and $R^{4C}$ together with a carbon atom form a divalent alicyclic hydrocarbon group having 4 to 20 carbon atoms if $R^{4B}$ and $R^{4C}$ bond with each other via the carbon atom, wherein
$R^3$ in the formula (1) comprises a group shown by formula (I-1),

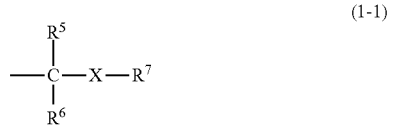

wherein
X represents an oxygen atom or a sulfur atom, each of $R^5$ and $R^6$ represents one of a hydrogen atom, an alkyl group having 1 to 20 carbon atoms, and an alkoxy group having 1 to 20 carbon atoms, and $R^7$ represents one of an alkyl group having 1 to 20 carbon atoms, an alkoxyalkyl group having 2 to 20 carbon atoms, an alicyclic hydrocarbon hydrocarbon group having 3 to 20 carbon atoms, an aryl group having 6 to 18 carbon atoms, and an aralkyl group having 7 to 19 carbon atoms, and wherein
$R^5$ and $R^7$ bond to form a heterocyclic structure having 3 to 20 carbon atoms together with the carbon atom that is bonded to $R^5$ and $R^7$.

8. The radiation-sensitive resin composition according to claim 7, wherein the group represented by $-CR^{4A}R^{4B}R^{4C}$ in the formula (1) comprises one of a tert-butyl group and a tert-amyl group.

9. The radiation-sensitive resin composition according to claim 7, wherein the resin (B) comprises a repeating unit shown by a formula (2),

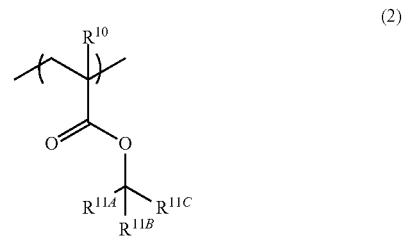

wherein $R^{10}$ represents a hydrogen atom or a methyl group, and wherein
- each of $R^{11A}$, $R^{11B}$, and $R^{11C}$ represents one of a linear or branched alkyl group having 1 to 4 carbon atoms and an alicyclic hydrocarbon group having 4 to 20 carbon atoms, or
- $R^{11A}$ represents one of a linear or branched alkyl group having 1 to 4 carbon atoms and an alicyclic hydrocarbon group having 4 to 20 carbon atoms and $R^{11B}$ and $R^{11C}$ are such that $R^{11B}$ and $R^{11c}$ together with a carbon atom form an alicyclic hydrocarbon group having 4 to 20 carbon atoms if $R^{11B}$ and $R^{11C}$ bond with each other via the carbon atom.

10. The radiation-sensitive resin composition according to claim 7, wherein n=1.

* * * * *